(12) United States Patent
Yonezawa et al.

(10) Patent No.: US 6,654,110 B2
(45) Date of Patent: Nov. 25, 2003

(54) IMAGE PICKUP APPARATUS AND DEFECT INSPECTION APPARATUS FOR PHOTOMASK

(75) Inventors: Makoto Yonezawa, Yokohama (JP); Haruhiko Kusunose, Yokohama (JP)

(73) Assignee: Lasertec Corporation, Yokohama (JP)

( * ) Notice: Subject to any disclaimer, the term of this patent is extended or adjusted under 35 U.S.C. 154(b) by 0 days.

(21) Appl. No.: 10/261,679

(22) Filed: Oct. 2, 2002

(65) Prior Publication Data

US 2003/0189703 A1 Oct. 9, 2003

(51) Int. Cl.$^7$ .............................................. G01N 21/88
(52) U.S. Cl. ................ 356/237.2; 356/237.4; 356/237.5
(58) Field of Search ................ 356/237.1, 237.2–237.5, 356/239.1–239.8, 432, 445; 250/559.44

(56) References Cited

U.S. PATENT DOCUMENTS

2002/0044277 A1    4/2002   Yonezawa

*Primary Examiner*—Richard A. Rosenberger
*Assistant Examiner*—Vincent P. Barth
(74) *Attorney, Agent, or Firm*—Oblon, Spivak, McClelland, Maier & Neustadt, P.C.

(57) ABSTRACT

The present invention has a configuration in which a line confocal optical system is formed and plural times of illumination by lines of lights are carried out. Particularly, in the present invention, the diffraction grating 32 produces the m×n number of sub beams. Further, the m×n number of sub beams are deflected by the acoustic optical element 33 so that their irradiation areas are to be continuous. Therefore, since the beam carries out scanning using the m×n number of sub beams, scanning can be completed in a short time.

12 Claims, 5 Drawing Sheets

IMAGE PICKUP APPARATUS AND DEFECT INSPECTION APPARATUS FOR PHOTOMASK

BACKGROUND OF THE INVENTION

1. Field of the Invention

The present invention relates to an image pickup apparatus having a high resolution and a high signal-to-noise (S/N) ratio using a confocal optical system, and a photomask defect inspection apparatus having such an image pickup apparatus.

2. Related Background Art

In a conventional photomask defect inspection apparatus, a photomask to be inspected has been scanned at a high speed by a light beam for illumination, a transmitted light through or a reflected light from the photomask has been received by a one-dimensional image sensor, and then output signals from the image sensor have been compared with data stored in a database or compared with each other to detect the presence of contaminants and defects of a light blocking pattern.

Another conventionally known technique for a defect inspection apparatus is that a transmitted light through or a reflected light from a photomask is received by a two-dimensional CCD camera, and output signals from light receiving elements of the CCD camera have been compared with data stored in a database or compared with each other to detect defects.

As integration and density of LSI become higher, a pattern of photomask becomes finer, thus placing strong demands for a photomask defect inspection apparatus with a higher resolution and defect detection signals with a higher S/N ratio. The above-mentioned technique of receiving a light from a photomask by a one-dimensional image sensor has the advantage of a relatively higher resolution because confocality is maintained. Charges stored in a light receiving element of the image sensor, however, is proportional to lighting time of an illumination light, that is, storage time of the charges. Accordingly, in the technique of high speed scanning using a light beam, time for a light from the photomask to enter to the image sensor is short, so an amount of the charges stored in the light receiving element become smaller, thus there are limits with regard to the S/N ratio of the defect detection signal.

On the other hand, in the technique of receiving a light from a photomask by a two-dimensional CCD camera, lighting time can be relatively longer, therefore a good performance can be obtained with respect to the S/N ratio. However, when taking a reflected image or a transmitted image of the photomask by the two-dimensional CCD camera, stray lights such as a flare or a glare enter to light receiving elements, thus there are limits to a resolution and to a defect inspection of a fine pattern.

Further, in order to optically inspect defects of a fine pattern, it is preferable to use a light having a short wavelength, that is, an ultraviolet light as an illumination light. However, with the ultra violet light, absorption by optical elements is large and sensitivity of a photodiode is low, there is a problem that a sufficient detection sensitivity is difficult to be obtained with a conventional defect inspection apparatus. Also, among types of defects are defects due to deposition of contaminants and pattern defects due to failure in accurate formation of a chrome light blocking pattern. If these types of defects can be distinguished, a defect inspection apparatus would be able to have wider applications.

A solution for the above problems is disclosed in U.S. Patent Publication No. US-2002-0044277-A1 (entitled: "Image Pickup Apparatus and Defect Inspection System for Photomask"). In the image pickup apparatus according to the above related art, an illumination light is projected as a line of illumination light through a spatial filter having plural slits which extend in a direction perpendicular to a direction of movement of a sample. Also, a transmitted light or a reflected light from the sample is received by an image sensor through a spatial filter having plural slits which also extend in a direction perpendicular to a direction of movement of a sample. Therefore, a line confocal optical system is configured, and stray lights such as a flare or a glare are significantly decreased to be able to take images of a high resolution.

Further, in this configuration, a moving speed of the sample and a line transfer speed of the image sensor are linked with each other. That is, the moving speed of the sample stage and the charges transfer speed of the image sensor is set so that the time interval during which the sample moves from a position into which an illumination light having passed through an i-th slit of a first spatial filter enters to a position into which an illumination light having passed through an adjoining i+1th slit enters, and the time interval during which the image sensor transfers the charges stored in a line of light receiving elements into which a light having passed through an i-th slit of a second spatial filter enters to a line of light receiving elements into which an illumination light having passed through an adjoining i+1st slit enters become equal to each other. Accordingly, the same portion of the sample is illuminated plural times, and charges generated by each illumination is accumulated, thus noise can be greatly reduced to significantly improve a S/N ratio. Consequently, both resolution and S/N ratio can be simultaneously improved, and it is possible to provide a defect inspection apparatus with a much higher accuracy by using an image pickup apparatus having such a high resolution and high S/N ratio as an image pickup optical system of a photomask defect inspection apparatus.

In the embodiment shown in FIG. 3 of the above-mentioned prior art, a laser light source, a diffraction grating, and abeam deflection device are used as a reflection-type image pickup optical system. The number of sub beams produced by the diffraction grating corresponds to the number of slits of the second spatial filter arranged in front of a second image sensor for receiving a reflected light. Therefore, in order to irradiate the whole of the slits of the second spatial filter by the sub beams, it is necessary to have the sub beams scan across the entire width of the slits. Accordingly, the scanning time becomes longer, thus the prior art has a problem of being unable to comply with the demand for a higher scanning.

On the other hand, AO deflection element (an acoustic optical element) is often used for the beam deflection device. In the acoustic optical element, ultrasonic pressure waves are provided with crystal to diffract an incident light by a diffraction grating consisting of the pressure waves. A diffraction angle is determined by the speed of sound in the crystal and the grating constant fixed by a frequency of the ultrasonic given. If the frequency of the ultrasonic is changed here, a deflection angle is changed, thereby enabling scanning using the laser beam. The frequency is changed at a constant rate during the scanning, and since the change also advances in the crystal at the speed of sound, the deflection angle gradually changes depending on the position of the crystal in the direction to which the sound wave advances. This is sometimes called cylindrical lens effect.

Due to this effect, the laser beam having done with scanning extends to be elliptical, which requires to be corrected. Also, a blanking interval which is a period during which the beam having done with scanning is moved back to the original angle at a high speed also takes a length of time required for the ultrasonic to pass through the crystal. The blanking interval takes about 7.5 micro second ($\mu$s) for a crystal with an ultrasonic path of 5 mm, of $TeO_2$ which can have a wide deflection angle. With high speed scanning performance of TDI (Time Delay & Integration) sensor having multitap output, it is easy to attain a image pickup speed of 6 $\mu$s per 1 scanning line. It is not practical if such high speed scanning takes the blanking interval of as long as 7.5 $\mu$s.

As in the foregoing, the conventional image pickup apparatus has the problem of taking long time for scanning using the laser beam, thus being unable to meet the demand for a higher scanning.

SUMMARY OF THE INVENTION

The present invention has been accomplished to solve the above problem, and an object of the present invention is thus to provide an image pickup apparatus enabling high speed scanning, and a defect inspection apparatus for photomask.

An image pickup apparatus according to the present invention is an image pickup apparatus having a sample stage moving sample whose image is to be taken in a first direction; a light source emitting a light beam; a diffraction grating generating m×n number of sub beams at predetermined intervals along a direction corresponding to the first direction and a second direction perpendicular to the first direction from the light beam; a beam deflection device deflecting the m×n number of sub beams in the first direction; an image sensor receiving a transmitted light or a reflected light from the sample, having plural light receiving elements arranged in a two-dimensional array along the first and the second directions, successively transferring the charges stored in each line of light receiving elements arranged along the first direction, line by line, at a predetermined line transfer speed, and successively outputting the charges stored in the light receiving elements; a spatial filter arranged between the sample stage and the image sensor, and having plural slits formed at a predetermined pitch along the second direction and extending in the first direction; and a drive control circuit controlling drive of the image sensor and the beam deflection device; wherein a reflected light or a transmitted light by the m×n number of sub beams scanning a surface of the sample enters into the image sensor through each slit of the spatial filter; the moving speed of the sample stage and the charge transfer speed of the image sensor are set so that the time interval during which the sample moves from a position into which an i-th line of the sub beam enters to a position into which an i+1-th line of the sub beam adjoining with the second direction enters, and the time interval during which the image sensor transfers the charges stored in a line of the light receiving elements into which a light having passed through an i-th slit of the spatial filter enter to a line of the light receiving elements into which an illumination light having passed through an adjoining i+1-st slit enters become equal to each other; and the drive control circuit controls drive of the beam deflection device so that irradiation areas formed by the movement of the m×n number of sub beams are to be continuous toward the first direction. In this configuration, a high resolution can be attained and the S/N ratio can be significantly improved; in addition, since the beam carries out scanning using the m×n number of sub beams, scanning can be completed in a short time. In a preferred embodiment, the drive control circuit controls drive of the beam deflection device so that irradiation areas formed by the movement of the m×n number of sub beams are to be continuous in the first direction in one scanning period.

Also, it is possible to have the beam scan more effectively when the drive control circuit controls drive of the beam deflection device so that irradiation areas formed by the movement of the m×n number of sub beams are to be continuous in the first direction during the time when a position into which an i-th line of the sub beam enters to a position into which an i+1-th line of the sub beam adjoining with the second direction enters.

Further, it is preferable that the drive control circuit moves the m×n number of sub beams in the first direction and also in the direction opposite to the first direction to carry out scanning. By scanning in this manner, serrated distortion of images can be reduced.

In a preferred embodiment, the beam deflection device is an acoustic optical element. The above mentioned image pickup apparatus is preferably used in a photomask defect inspection apparatus which inspects defects of a photomask.

The present invention will become more fully understood from the detailed description given hereinbelow and the accompanying drawings which are given by way of illustration only, and thus are not to be considered as limiting the present invention.

DESCRIPTION OF THE PREFERRED EMBODIMENTS

In the followings, preferred embodiments of the present invention will be described in detail with reference to the drawings.

Figure 1:
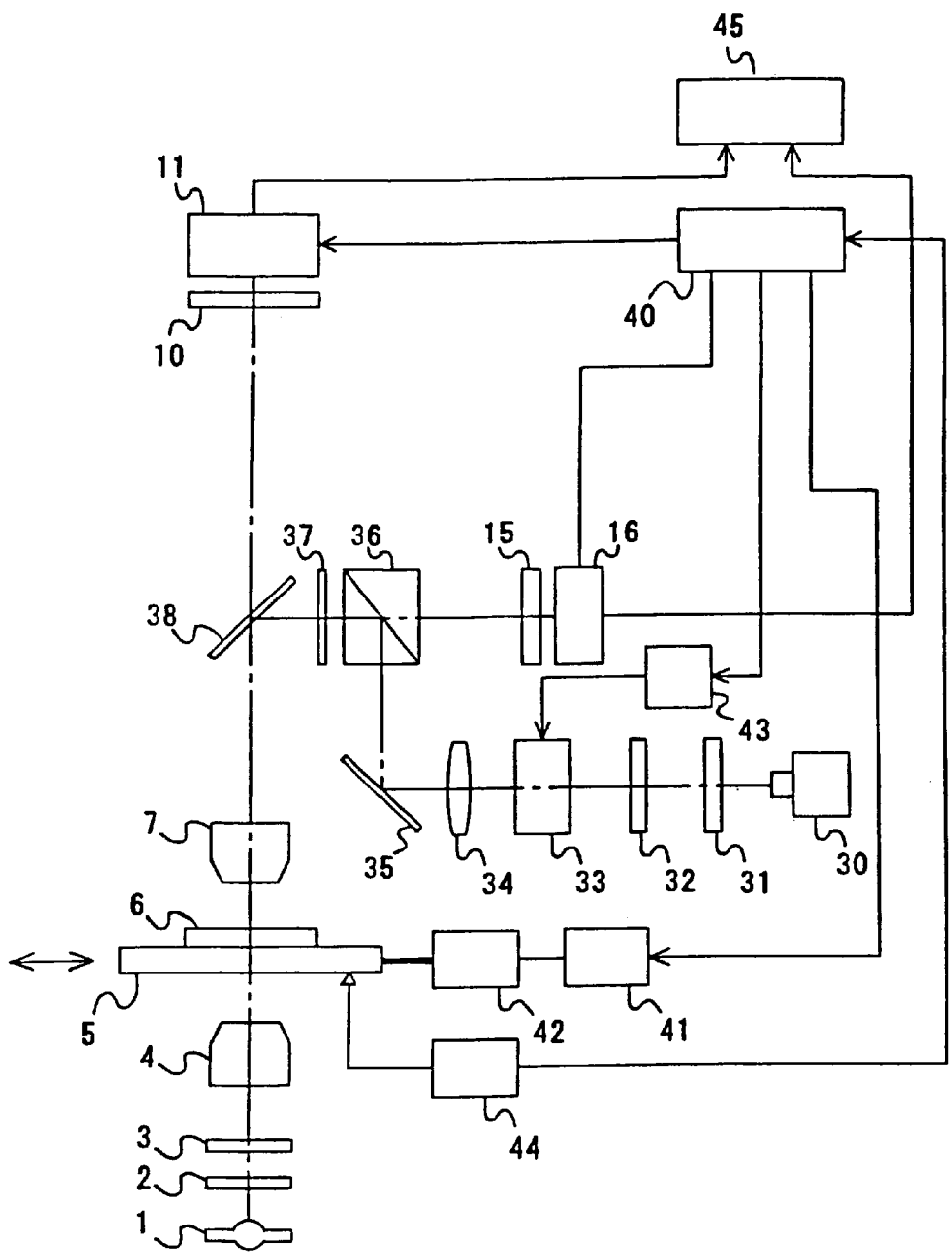
FIG. 1 is a block diagram showing an image pickup apparatus and a defect inspection apparatus for photomask according to the present invention.

FIG. 1 is a block diagram to show an image pickup apparatus and a photomask defect inspection apparatus according to the present invention. In the example here, a system in which transmission-type inspection and reflection-type inspection can be individually or simultaneously carried out will be explained.

In the first place, an image pickup by a transmitted light will be described.

A first light source 1 such as a mercury lamp, for example, is used as an illumination light source, a wavelength filter 2 passing only a light having a wavelength of 365 nm is arranged in the front of the first light source 1, and a first spatial filter 3 is arranged next to the wavelength filter 2. In the first spatial filter 3, plural slits extending in a first direction which is perpendicular to a paper surface are configured at a predetermined pitch. An illumination light having passed through the slits of the spatial filter 3 passes through an illumination lens 4 and then enters into a sample 6 supported on a sample stage 5 as a line of parallel light beams. In this example, the sample 6 is a photomask which is composed of a transparent substrate on which a chrome light blocking pattern is formed. The sample stage 5 moves at a predetermined speed in the direction of the arrows, that is, a second direction perpendicular to the extending direction of the slits of the spatial filter 3. Therefore, the photomask 6 is illuminated plural times by plural lines of the illumination light.

The lines of illumination light having passed through the photomask 6 pass through an objective lens 7 and a dichroic mirror 38, and then pass through a second spatial filter 10 to enter into a first image sensor 11. The second spatial filter 10 is arranged in front of the first image sensor 11 and is formed at a predetermined pitch with plural slits extending in the first direction perpendicular to the paper surface in the same way as the filter spatial filter 3. Further, the second spatial filter 10 is arranged so that the lines of transmitted light having passed through the slits of the first spatial filter 3 and transmitted through the photomask pass through the slits.

The first image sensor 11 is an image sensor having plural light receiving elements arranged in a two-dimensional array in the first and the second directions. In this example, 2048 lines of light receiving elements in the first direction and 200 lines of light receiving elements in the second direction are arranged. The second direction may be called a line direction. The image sensor 11 has 200 lines of light receiving elements, with one line arranged 2048 light receiving elements. The first spatial filter 3, the photomask 6, and the first image sensor 11 are arranged in a conjugate relationship. Therefore, an image of the slits of the first spatial filter 3 is projected on the photomask 6, and a transmitted image of the photomask 6 is projected on the first image sensor 11 through the object lens 7. In this configuration, a line confocal optical system is formed to further increase a resolution. It is also possible to use a so-called TDI sensor in which an image sensor and a spatial filter are formed integrally, designed so that lights are to enter into only light receiving elements of specific lines.

In the next place, an image pickup by a reflected light will be described.

As a light source of a reflection type image pickup apparatus, an argon laser 30 generating a light beam having a wavelength of 488 nm is used, for example. A laser beam emitted from the argon laser 30 is converted into an expanded parallel luminous flux by a expander 31.

Further, in the present embodiment, the expanded parallel luminous flux is diffracted both in the first direction perpendicular to a paper surface and the second direction corresponding to a moving direction of the sample by a diffraction grating 32. That is, the diffraction grating 32 generates sub beams of m number in the first direction and n number in the second direction, which is, m×n number of sub beams in two-dimensional arrangement. The diffraction by the diffraction grating 32 will be detailed later. The m×n number of sub beams enter to an acoustic optical element 33 to be deflected by a predetermined deflection frequency in the first direction. The deflection frequency of the acoustic optical element does not necessarily have to be equal to the line transfer frequency of the image sensor 16, but is preferably set to be 1/a whole number (including equal value) of the line transfer frequency of the image sensor 16. Here, it is supposed that the deflection frequency of the acoustic optical deflection element is 1/k of the line transfer speed of the image sensor 16.

The sub beams travel via a lens 34, a full reflection mirror 35, a deflection beam splitter 36, and a ¼wavelength plate 37 to enter the dichroic mirror 38. In this example, a wavelength filter 2 passing a light having a wavelength of 365 nm is arranged in front of the light source 1 for pickup of a transmitted image; thus the dichroic mirror 38 is used to separate a transmitted light and a reflected light from the sample. The m×n number of sub beams having a wavelength of 488 nm are reflected by the dichroic mirror 38 and then enter to be focused as a spot into the photomask 6, which is the sample, through the object lens 7. Therefore, on the photomask 6, the m×n number of light spots arranged at intervals of a predetermined pitch are formed both along the second direction and along the first direction. The sample 5 is scanned by these light spots at a frequency of 1/k of the line transfer frequency in the first direction perpendicular to the moving direction of the photomask. When the angle of the deflection by the acoustic optical element 33 in one line transfer period is set to be equal to the interval of m number of sub beams in the first direction, each portion of the photomask is scanned n number of times by the m×n number of light beams.

A reflected light from the surface of the sample 6 travels via the object lens 7, is reflected at the dichroic mirror 38, passes through the ¼wavelength plate 37, and then enters to the deflection beam splitter 36. Since the reflected light has passed through the ¼wavelength plate twice, the deflection plane is rotated in 90 degrees. Accordingly, the reflected light passes through the deflection beam splitter 36 and enters to the second spatial filter 15. Here, the optical elements of the reflection optical system are set so that a reflected light from each light spot which is formed by the m×n number of sub beams scanning the sample along the first direction is to enter into each slit of the spatial filter 15 which is positioned in a conjugate relationship with the sample. Therefore, each slit of the spatial filter 15 is scanned by the m×n number of the reflected lights oscillating in the first direction, and the reflected lights respectively passes through the slits to enter to each line of light receiving elements of the second image sensor 16 which is located in the back of the spatial filter 15. That is, each line of light receiving elements of the second image sensor corresponding to each slit of the spatial filter 15 is scanned by the sub beams deflected by the acoustic optical element 33. It is also possible to use a so-called TDI sensor in which an image sensor and a spatial filter are formed integrally, designed so that a light is to enter into only light receiving elements of specific lines.

Next, drive control of the image pickup apparatus will be described hereinbelow. A synchronization signal generation circuit 40 is provided for drive control, and drive signals are transmitted from the synchronization signal generation circuit 40 to control each device. A stage feed pulse is supplied from the synchronization signal generation circuit 40 with the motor driver 41, and a stage drive motor 42 is driven based on drive signals from the motor driver 41, and the sample stage 5 is driven in the first and second directions.

Line shift pulses are supplied from the synchronization signal generation circuit 40 with the first and second image sensors 11 and 16, and charges stored in the light receiving elements are successively transferred line by line at a line transfer speed of, for example, 40 kHz., and then serially outputted. Further, drive pulses of 40 kHz are supplied from the synchronization signal generation circuit 40 with an acoustic optical element control circuit 43 controlling drive of the acoustic optical element 33, and the acoustic optical element 33 is controlled by the same frequency as the line transfer speed of the image sensor. Therefore, when scanning using m×n number of sub beams, the sample and the light receiving elements are scanned n times.

In the present embodiment, it is necessary to accurately synchronize the moving speed of the sample and the line transfer speed of the image sensors. Therefore, in this example, a stage position detection apparatus 44 such as a laser interferometer is used to detect the position of the sample stage 5 and supply the result to the synchronization signal generation circuit 40. In the synchronization signal generation circuit, the frequency of the line shift pulses for the image sensors is corrected in accordance with the detected position of the sample stage so that the line transfer speed of the image sensors and the moving speed of the sample stage correspond to each other. By using such a feedback system, even if a slight error in speed occurs in the movement of the stage, it is possible to make the transfer speed of the image sensors and the moving speed of the stage accurately correspond.

It is possible to detect the existence of contaminants by supplying the outputs of the first and second image sensors 11 and 16 to a defect detection circuit 45, using an adder to generate a sum signal of the output signals of the image sensors, and comparing the sum signal with a threshold value.

Figure 2:
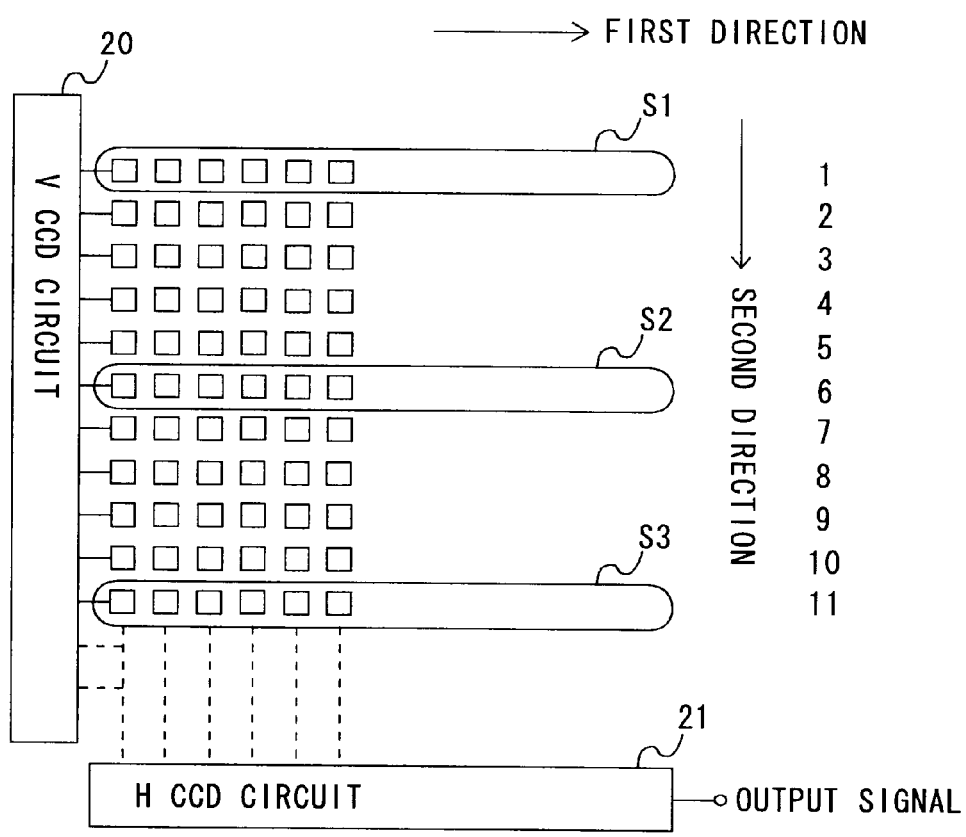
FIG. 2 is a diagram showing a relationship between an image sensor and a spatial filter.

Then, a relationship between the image sensor and the spatial filter arranged in front of the same will be described in the following. FIG. 2 diagrammatically shows a relationship between an array of light receiving elements of the second image sensor 16 and an array of slits of the second spatial filter arranged in front of the second image sensor 16. The second image sensor 16 has 2048 light receiving elements arranged along a direction corresponding to a first direction (H-direction) to form one line, and 200 lines of light receiving elements are arranged in a second direction (V-direction) perpendicular to the first direction.

Slits S1 to Sn of the spatial filter 15 are arranged every five lines, that is, on the third line, eighth line, thirteenth line, etc. of the image sensor 16. Therefore, reflected lights from the photomask which is a sample enter only to the light receiving elements of the third line, eighth line, thirteenth line ... (5l+3) ... -th line of the image sensor. Accordingly, the lights enter only to the light receiving elements in the 5l+1st lines of the light receiving elements, and the light receiving elements positioned between the above lines of the light receiving elements function to transfer charges which have been transferred to the next lines of light receiving elements. To the image sensor 16, a V-direction CCD circuit 20 and H-direction CCD circuit 21 are connected. The charges occurring at each line of light receiving elements are successively transferred line by line to the next light receiving elements by the control of the V-direction CCD circuit 20, while the charges stored at each line of light receiving elements are successively and serially output by the drive control of the H-direction CCD circuit 21.

In the example here, the moving speed of the sample stage and the transfer speed in the V-direction (corresponding to the second direction) of the image sensor correspond to each other. That is, a time period from when the sample is scanned by the i-th lines of sub beams to when scanned by the adjoining i+1-th lines of sub beams, and a time period during which charges stored in lines of light receiving elements corresponding to the i-th slits of the spatial filter 15 of the light receiving side are transferred to the adjoining i+1-th slits, are set to be equal to each other. In this configuration, the effect equivalent to that when the sample is scanned plural times by lines of illumination lights can be obtained; on the other hand, since the light receiving elements of the image sensors have charge storing ability, charges produced by each scanning are successively build up. Consequently, noise occurring due to an optical element and so on can be greatly reduced, thereby being able to output signals with a high S/N ratio and high sensitivity. In addition, since the charge storing ability of the light receiving elements is positively utilized, even if an ultraviolet light with a high absorption for light receiving elements is used, output signals with a high output level and high sensitivity can be produced.

Figure 3:
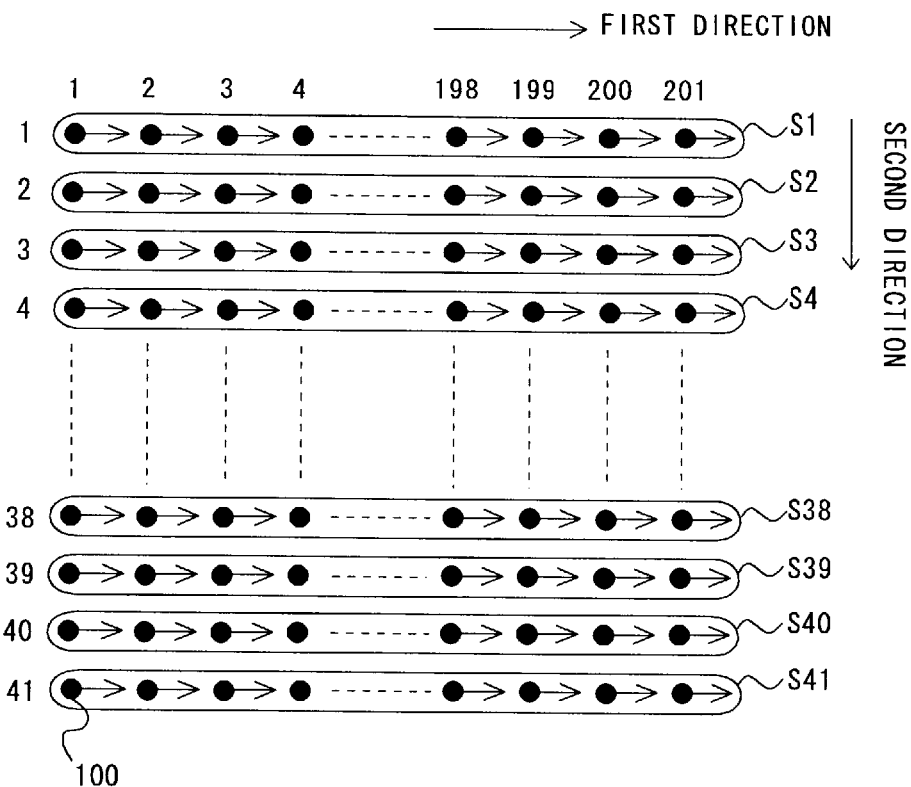
FIG. 3 is a diagram explaining irradiation of laser beam.

FIG. 3 shows irradiation of laser beam. In an image pickup apparatus according to the present invention, an image is formed while charges are moved in 100 to 200 lines toward the second direction (V-direction); thus, all the pixels are to be filled with illumination lights which have scanned during that time. The second filter 15 has openings at one line in every five lines of 200 lines of light receiving elements in the second direction. Therefore, in the image sensor 16, an image is taken by 40 lines of light receiving elements. In the embodiment according to the present invention, the 40 lines of light receiving elements are effectively illuminated.

As in the foregoing, the diffraction grating 32 diffracts a laser beam in m×n number of a two-dimensional arrangement. As shown in FIG. 3, the diffraction grating generates 41×201, which is, 8241 points of sub beams 100, for example. Usually, the points of the grating are set to be an odd number times an odd number. In the 41×201 number of sub beams 100, a pitch of 41 sub beams corresponding to the second direction is equal to an interval of the second spatial filter 15. Then, as shown in FIG. 3, the 8241 points of sub beams 100 are moved all at once to the first direction by the acoustic optical element 33. The sub beams are moved to positions adjacent to original positions of the next sub beams and then moved back to their original positions for 41 irradiation areas formed by the movement of the sub beams to be continuous. Here, when the sub beams are moved back to their original positions, it is preferable to cut laser beams entering to the acoustic optical element using electro-optic (EO) elements.

Figure 4:
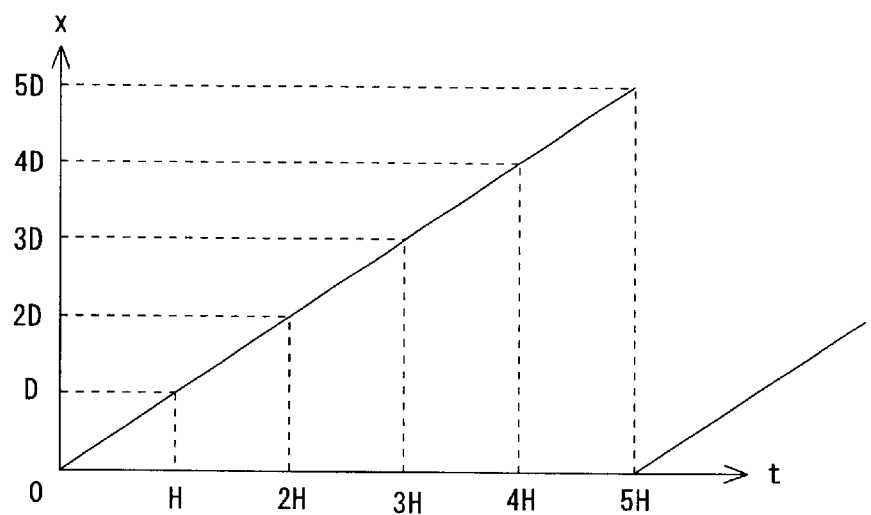
FIG. 4 is a timing chart showing scanning by a laser beam.

FIG. 4 is a timing chart showing scanning by a laser beam. FIG. 4 shows changes in a striking positions of one of the sub beams 100 by time series. A vertical axis represents a position in the first direction. A position 0 of the vertical axis represents a position where the sub beam 100 is originally positioned. A position D of the vertical axis represents a position where the moved sub beam 100 reaches after 1h of a time period. The scanning speed of the acoustic optical deflection element is adjusted so that the position D becomes equal to a position adjacent to an original position of the next sub beam. A horizontal axis represents time. Time H represents one scanning period. It is the reciprocal of the above-mentioned line transfer frequency. As shown in FIG. 4, the sub beam 100 is moved to the position D in one scanning period. At the time of starting the next scanning period, scanning is started from the position D. Since a deflection frequency of the acoustic optical deflection element is set to be 1/k of the line transfer frequency, after scanning during kH period, the sub beam 100 is moved back to its original position 0 to start the next scanning from that position. While FIG. 4 shows changes in a striking position of one of the sub beams 100, all of the 8241 sub beams are moved similarly.

As explained in the foregoing, in an image pickup apparatus according to the first embodiment of the present invention, the m×n number of two-dimensional sub beams are formed by the diffraction grating, and by moving the sub beams all at once, the moving distance of each of the sub beams can be shortened; consequently, high speed scanning can be attained.

Figure 5:
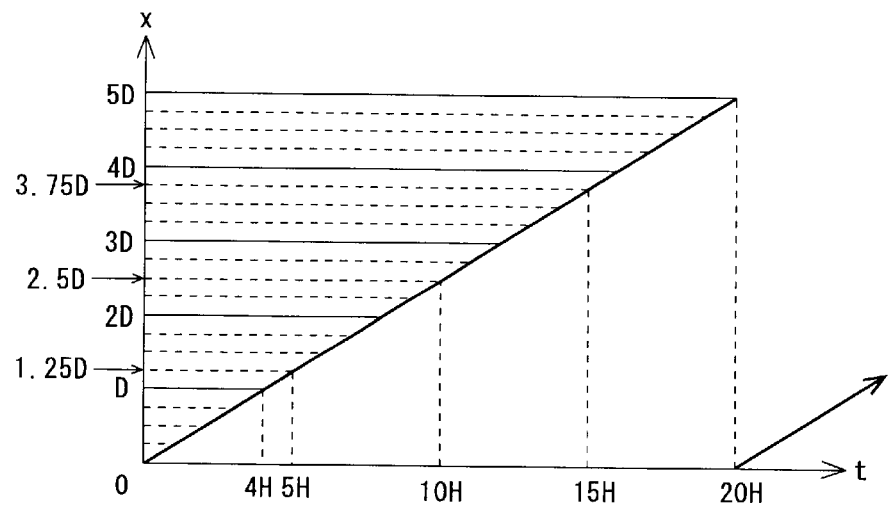
FIG. 5 is a timing chart showing scanning by another laser beam.
Figure 6:
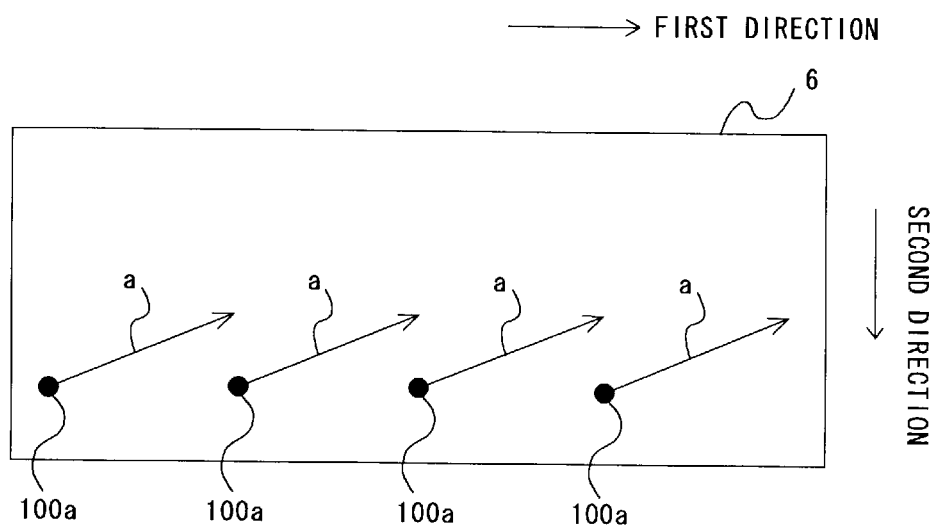
FIG. 6 is a diagram explaining a movement of a laser beam on a sample.

FIG. 5 is a timing chart showing scanning by a laser beam in an image pickup apparatus according to the second embodiment of the present invention. In this embodiment, the above-mentioned value k is determined to be 20, and the amount scanned by one scanning line is ¼ of an interval between spots of the adjoining sub beam. That is, as shown in FIG. 5, in time period, 5H of 5 scanning lines, an additional ¼ more distance of the interval between spots of the adjoining sub beam is scanned. During the above period, while charges on TDI again reach a line having some sensitivity, a position of the sub beam which have carried out scanning corresponds to a position where the next beam reaches after 1H when the sub beam is at its original point 0, and then scanning is started from that position. Accordingly, the distance in which the sub beam is moved in one scanning period can reduced to be ¼ compared to the case described in the first embodiment of the present invention. When illuminating in this way, even if a time interval of scanning lines is as short as 6 μs, a period of laser scanning can be lengthen to be 20 times longer; thus the effect of a blanking interval is reduced to be ½₀.

In the second embodiment of the present invention, it is possible to carry out scanning by the beam more effectively because the drive control circuit controls drive of the acoustic optical element so that irradiation areas formed by the movement of the m×n number of sub beams are to be continuous in the second direction during the time when a position into which an i-th line of the sub beam enters to a position into which an i+1-th line of the sub beam adjacent to the first direction enters.

An image pickup apparatus according to the third embodiment of the present invention is provided with a means of reducing an image distortion. First, a factor causing a distortion of an image will be described. A spot of a laser beam is moved to the first direction. Here, at the same time, the sample 6 is continuously moved to the second direction. Consequently, a spot 100a of the laser beam obliquely scans on the sample 6. That is, the spot 100a of the laser beam is moved to the first direction and also to the direction opposite to the second direction. Then, the spot 100a of the laser beam reflected from or transmitted through the sample 6 is detected by a CCD element of the image sensor 16. Here, an incident light detected by the CCD element corresponds to the portion which has been obliquely scanned on the sample 6. On the other hand, in the CCD element, charges are moved in every scanning period. Therefore, the incident light corresponding to the portion which has been obliquely scanned is detected as a portion in which a region parallel to the first direction has been scanned. Accordingly, with a repeated period of an interval between spots of the sub beams adjacent to the first direction, an image is distorted to have serration.

In order to prevent the above disadvantage, an image pickup apparatus according to the third embodiment of the present invention has a configuration in which a laser is moved back to the opposite direction after scanning to a certain extent in the first direction. In this way, a direction of serration is reversed; consequently, a smooth image can be obtained.

Figure 7:
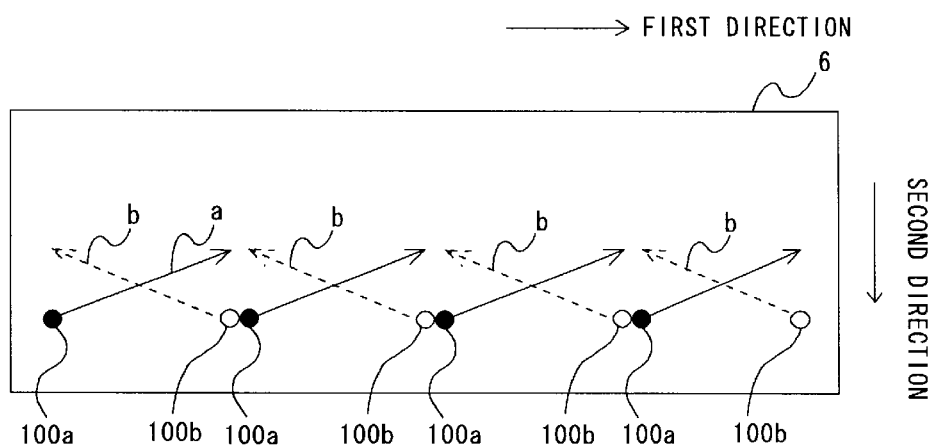
FIG. 7 is a diagram explaining a movement of a laser beam on a sample.

FIG. 7 is a diagram explaining a movement of a laser beam on a sample. As shown in FIG. 7, the sub beam 100a not only scans to the direction indicated by an arrow a (which will be referred to hereinafter as a forward direction) but also has a sub beam 100b scan to the direction indicated by an arrow b (which will be referred to as a reverse direction). That is, scanning by the sub beam 100a in the forward direction includes moving the sub beam 10Db to the direction opposite to the first direction and to the direction opposite to the second direction at one time.

Figure 8:
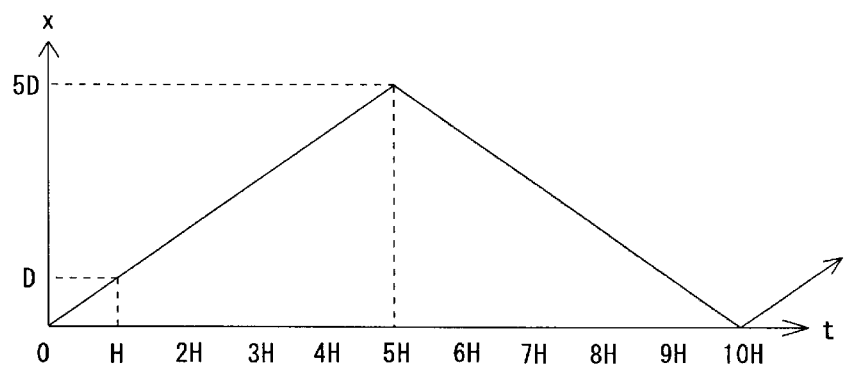
FIG. 8 is a timing chart showing scanning by another laser beam.

Specifically, the operation is attained by controlling the acoustic optical element 33 using an acoustic optical element control circuit 43. For example, the control is carried out in accordance with the timing chart shown in FIG. 8. In the example here, in a first scanning period (0 to H), a following scanning period (H to 2H), and another following scanning period (2H to 3H), the sub beam 10a carried out scanning in the forward direction. In a following scanning period (3H to 4H), the sub beam 100b carries out scanning in the reverse direction. Then, in scanning period (4H to 5H), a following scanning period (5H to 6H), and another following scanning period (6H to 7H), the sub beam 10a carries out scanning in the forward direction. In a following scanning period (7H to 8H), the sub beam b carried out scanning in the reverse direction. By scanning in this manner, a serrated distortion of images can be reduced.

A fourth embodiment of the present invention relates to a defect inspection apparatus for a photomask having an image pick up apparatus described in the first to third embodiments. A configuration of the photomask defect inspection apparatus is described in detail in U.S. patent application Ser. No. 09/973,780 (entitled: "Image Pickup Apparatus and Defect Inspection System for Photomask"), for example. In the example here, two image pickup heads are used to detect defects by die-to-die comparison. Most photomasks have a plurality of the same dies, that is, chips, therefore defects can be detected by using two image pickup heads of the same configuration to take images of two adjoining mask patterns by a die-to-die or chip-to-chip relationship and then comparing the results.

While the above example describes a case where the m×n number of sub beams are used when detecting a reflected light from the sample, it is not restricted thereto, and they can be also used when detecting a transmitted light from a sample. In this case, the first light source 1, the wavelength filter 2, the first spatial filter 3, and the illumination lens 4 shown in FIG. 1 are replaced with the argon laser 30, the expander 31, the diffraction grating 32, the acoustic optical element 33, and the lens 34.

Also, the sub beams formed by the diffraction grating 32 do not necessarily arranged in a uniform manner over all the region to strike, as long as they are formed in a two-dimensional manner.

Though the forth embodiment of the present invention explains a case where the image pickup apparatus is applied to defect inspection for a photomask, it is not restricted thereto, and the apparatus can be applied to image pick up or defect inspection of patterns configured on various substrates. For example, the image pickup apparatus according to the present invention can be applied to an image pickup apparatus or defect inspection apparatus for a pattern configured on the surface of a semiconductor wafer in a manufacturing processes of a semiconductor device. Further, the confocal optical system can be applied to inspection of evenness of a substrate surface or warping of a substrate and so on since a focal depth is relatively short; therefore, it can be also used for defect inspection of a sample with no pattern configured, that is, for example, photomask blanks or semiconductor wafer blanks. Also, the system can be used for defect inspection of a substrate in a liquid crystal display apparatus.

As explained in the foregoing, according to the present invention, it is possible to provide an image pickup apparatus enabling high speed scanning and a defect inspection apparatus for photomask.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. An image pickup apparatus, comprising:
    a sample stage configured to move at a moving speed a sample whose image is to be taken in a first direction;
    a light source configured to emit a light beam;
    a diffraction grating configured to generate m×n number of sub beams at predetermined intervals along a direction corresponding to the first direction and a second direction perpendicular to the first direction from said light beam, wherein said m×n number of sub beams include a reflected light or a transmitted light configured to scan a surface of said sample;
    a beam deflection device configured to deflect said m×n number of sub beams in the first direction;
    an image sensor configured to receive a transmitted light or a reflected light from said sample, having a plurality of light receiving elements arranged in a two-dimensional array along the first and second directions, to successively transfer at a charge transfer speed charges stored in a line of each of said plurality of light receiving elements arranged in the first direction, line by line, at a predetermined line transfer speed, and to successively output the charges stored in said plurality of light receiving elements;
    a spatial filter arranged between said sample stage and said image sensor, and having a plurality of slits formed at a predetermined pitch along the second direction and extending in the first direction, said reflected light and said transmitted light entering into said image sensor through each of said plurality of slits, and a first time interval being defined by the time necessary for said sample to move at said moving speed from a first position into which an i-th line of said m×n number of sub beams enters, to a second position into which an i+1-th line of said m×n number of sub beams adjacent to the second direction enters, and a second time interval is defined by the time necessary for said image sensor to transfer at said charge transfer speed the charge stored in the line of said plurality of light receiving elements into which a light having passed through an i-th slit of said plurality of slits of said spatial filter enters, to the line of said plurality of light receiving elements into which an illumination light having passed through an adjoining i+1th slit of said plurality of slits enters; and
    a drive control circuit configured to control a driving of said image sensor and said beam deflection device, said image sensor being controlled such that said first and second time intervals are equal, and said beam deflection device being controlled such that a movement of said m×n number of sub beams forms irradiation areas that are continuous in the first direction.

2. The image pickup apparatus according to claim 1, wherein said drive control circuit controls said beam deflection device such that irradiation areas formed by a movement of said m×n number of sub beams are continuous in the first direction in a scanning period.

3. The image pickup apparatus according to claim 1, wherein said drive control circuit controls said beam deflection device such that irradiation areas formed by a movement of said m×n number of sub beams are continuous in the first direction during a time when a third position into which an i-th line of said m×n number of sub beams enters to a fourth position into which an i+1-th line of said m×n number of sub beams adjacent to the second direction enters.

4. The image pickup apparatus according to claim 1, wherein said drive control circuit moves said m×n number of sub beams in the first direction and also in a direction opposite to the first direction to perform scanning.

5. The image pickup apparatus according to claim 1, wherein said beam deflection device comprises an acoustic optical element.

6. The image pickup apparatus according to claim 1, further comprising a defect inspection device configured to detect defects of a photomask as the sample.

7. An image pickup method, comprising:
    moving a sample by a sample stage whose image is to be taken in a first direction;
    emitting a light beam from a light source;
    generating a m×n number of sub beams by a diffraction grating at predetermined intervals along a direction corresponding to the first direction and a second direction perpendicular to the first direction from said light beam;
    deflecting via a beam deflecting device said m×n number of sub beams in the first direction;
    receiving a transmitted light or a reflected light by an image sensor from said sample, said image sensor having a plurality of light receiving elements arranged in a two-dimensional array along the first and second directions;
    successively transferring charges stored in a line of each of said plurality of light receiving elements arranged in the first direction, line by line, at a predetermined line transfer speed;
    successively outputting the charges stored in said plurality of light receiving elements;
    filtering said m×n number of sub beams via a spatial filter arranged between said sample stage and said image sensor, wherein said spatial filter has a plurality of slits formed at a predetermined pitch along the second direction and extending in the first direction; and
    controlling a driving of said image sensor and said beam deflection device,
    wherein a reflected light or a transmitted light of said m×n number of sub beams scanning a surface of said sample enters into said image sensor through each of said plurality of slits of said spatial filter,
    wherein a moving speed of said moving step and a charge transfer speed of said transferring step are set such that a first time interval during which said sample moves from a first position into which an i-th line of said m×n number of sub beams enters, to a second position into which an i+1-th line of said m×n number of sub beams adjacent to the second direction enters, and a second time interval during which said transferring step to transfer the charge stored in the line of said plurality of light receiving elements into which a light having passed through an i-th slit of said plurality of slits of said spatial filter enters, to the line of said plurality of light receiving elements into which an illumination light having passed through an adjoining i+1th slit of said plurality of slits enters, become equal to each other, and wherein said controlling step controls said beam deflection device such that irradiation areas formed by a movement of said m×n number of sub beams are continuous in the first direction.

8. The image pickup process according to claim 7, wherein said controlling step controls said beam deflection device such that irradiation areas formed by a movement of said m×n number of sub beams are continuous in the first direction in a scanning period.

9. The image pickup process according to claim 7, wherein said controlling step controls said beam deflection device such that irradiation areas formed by a movement of said m×n number of sub beams are continuous in the first direction during a time when a third position into which an i-th line of said m×n number of sub beams enters to a fourth position into which an i+1-th line of said m×n number of sub beams adjacent to the second direction enters.

10. The image pickup process according to claim 7, wherein said controlling step moves said m×n number of sub beams in the first direction and also in a direction opposite to the first direction to carry out scanning.

11. The image pickup process according to claim 7, wherein said beam deflection device comprises an acoustic optical element.

12. The image pickup process according to claim 7, further comprising detecting defects of a photomask as the sample.

* * * * *

UNITED STATES PATENT AND TRADEMARK OFFICE
CERTIFICATE OF CORRECTION

PATENT NO.    : 6,654,110 B2
DATED         : November 25, 2003
INVENTOR(S)   : Yonezawa et al.

It is certified that error appears in the above-identified patent and that said Letters Patent is hereby corrected as shown below:

<u>Title page,</u>
Item [30], should read:
-- [30]    Foreign Application Priority Data
Apr. 5, 2002 (JP) ………………………….. 2002-103204 --

Signed and Sealed this

Ninth Day of March, 2004

JON W. DUDAS
*Acting Director of the United States Patent and Trademark Office*